United States Patent [19]

Friedman

[11] Patent Number: 5,116,603
[45] Date of Patent: May 26, 1992

[54] ORAL ANTIFUNGAL PREVENTATIVE, AND METHOD OF USE

[75] Inventor: Michael Friedman, Jerusalem, Israel

[73] Assignee: Yissum Research Development Company of the Hebrew University of Jerusalem, Jerusalem, Israel

[21] Appl. No.: 465,786

[22] Filed: Jan. 18, 1990

Related U.S. Application Data

[63] Continuation-in-part of Ser. No. 304,092, Jan. 31, 1989, abandoned.

[51] Int. Cl.⁵ .................. A61K 6/00; A61K 31/74; A61K 31/745; A61K 31/78
[52] U.S. Cl. ........................... 424/53; 424/49; 514/900; 514/902
[58] Field of Search ............. 424/78, 81, 83, 53, 424/49; 514/900, 902, 953

[56] References Cited

U.S. PATENT DOCUMENTS

| | | | |
|---|---|---|---|
| 2,972,545 | 2/1961 | Briskin | 514/781 |
| 2,984,639 | 5/1961 | Stamberger et al. | 260/32.4 |
| 3,312,594 | 4/1967 | Cyr et al. | 167/82 |
| 3,394,001 | 1/1976 | Watson | 424/83 |
| 3,431,208 | 3/1969 | Bailey | 252/106 |
| 3,749,769 | 7/1973 | Sugiyama | 424/61 |
| 3,956,480 | 5/1976 | Dichter et al. | 424/78 |
| 4,315,779 | 2/1982 | Heyd et al. | 106/35 |
| 4,339,430 | 7/1982 | Gaffar | 424/54 |
| 4,374,824 | 2/1983 | Wahmi | 424/49 |
| 4,438,011 | 3/1984 | Howes | 134/42 |
| 4,459,277 | 7/1984 | Kosti | 424/49 |
| 4,725,440 | 2/1988 | Ridgway | 424/49 |
| 4,925,668 | 5/1990 | Khan et al. | 427/2 |
| 4,952,411 | 8/1990 | Fox, Jr. et al. | 514/635 |

FOREIGN PATENT DOCUMENTS

| | | |
|---|---|---|
| 1175355 | 10/1984 | Canada . |
| 6055397 | 11/1981 | Fed. Rep. of Germany . |
| 59-216822 | 12/1984 | Japan . |
| 8702580 | 5/1987 | PCT Int'l Appl. . |
| 990957 | 5/1965 | United Kingdom . |

OTHER PUBLICATIONS

Friedman, "Plaque Inhibition by Sustained Release of Chlorhexide", J. Dental Res. Nov. 1985.
Soskolne, W. A. et al., "New Sustained Release Dosage form of Chlorhexidine for Dental Use", J. Periodontal Res. 18:330-336, (1983).
Friedman, "New Sustained Release form of Chlorhexidine for Denteal Use", J. Periodont Res. 17:323-328 (1982).
Kostiala, I. et al., Acta Odontol. Scand. 37:87-101 (1979).
Budtz-Jörgensen, E. et al., Community Dent. Oral Epidemiol. 3:115 (1975).
Odds, F. C., CRC Crit Rev. Microbiol. 15: 1-5 (1987).
Lehner, T. in Clin. Aspects of Immunol., P.G.H. Gell eds. et al., 3rd edition, Blackwell Scientific Public, Oxford, 1975, pp. 1387-1427.
Friedman, M. et al., IADR Prog. and Abstr. 59:905 (1980), No. 72.
Friedman, M. et al., J. Dent. Res. 64:1319-1321 (1985).
Bossche, H. V., CRC Crit. Rev. Microbiol. 15:57-72 (1987).
Kirk-Othmer Encyclopedia of Chemical Technology, 2nd ed. (vol. 2, pp. 632-635).
Kanig, J. L. et al., J. Pharm. Sci. 51:77-83 (1962).
Friedman, M. et al., J. Cont. Rel. 1:157-160 (1984).

Primary Examiner—Jeffrey E. Russel
Attorney, Agent, or Firm—Sterne, Kessler, Goldstein & Fox

[57] ABSTRACT

The invention relates to an oral composition for prevention of mycotic infections of the oral cavity comprising an antifungal compound embedded in a sustained release carrier such as a cellulosic polymer or a hydrophobic polymer, and a method for use of said composition in preventing microfungal infections in the oral cavity. The invention also provides for the supplementation of said oral composition with an adhesive and a plasticizer to increase antifungal effectiveness.

9 Claims, No Drawings

ORAL ANTIFUNGAL PREVENTATIVE, AND METHOD OF USE

CROSS-REFERENCE TO RELATED APPLICATIONS

This application is a continuation-in-part of U.S. patent application Ser. No. 07/304,092 (filed on Jan. 31, 1989), now abandoned.

FIELD OF THE INVENTION

The invention is directed to an antimycotic composition for the prevention of microfungal infections of the oral cavity and to a method for using said composition in treating mycotic diseases of the oral cavity caused by microfungi.

BACKGROUND OF THE INVENTION

Microfungi can be classified as yeasts and filamentous fungi. Microfungi are capable of causing a variety of diseases in the oral cavity and the surrounding area. Mycotic diseases may arise as part of a systemic microfungal infection or may be derived from an independent infection which establishes in the oral cavity. Oral mycoses and their treatment are an important problem in oral medicine and have been reviewed in Kostiala, I. et al., *Acta Odontol. Scand.* 37:87-101 (1987), incorporated herein by reference.

Many factors can predispose a patient to an opportunistic microfungal infection in the oral cavity. For example, general debilitation or poor oral hygiene are predisposing factors. Patients who are being treated with antibiotics, steroids, or cytostatic therapy, patients with AIDS, diabetes mellitus or other immunodeficiency or hormonal diseases, patients with malignant tumors or a hematogenous disorder are all at a high risk for opportunistic fungal infections. In addition, certain age groups such as infants, the elderly, and pregnant women are at a higher risk of oral fungal infections.

Mechanical trauma from an ill-fitted prosthesis is also a major cause of oral microfungal infections. One report estimated that Candida was involved in 60% of the cases of "denture sore mouth" (denture stomatitis) in the elderly (Budtz-Jörgensen, E. et al., *Community Dent. Oral Epidemiol.* 3:115 (1975)). Denture stomatitis appears to be a manifestation of a cell-mediated hypersensitivity reaction to the microfungal infection.

It is important to treat oral mycotic infections as soon as possible. Untreated infections may become the foci for systemic dissemination of the yeast or fungus, with potentially fatal results in severely compromised patients. For example, disseminated candidosis is the second most common opportunistic infection in patients with AIDS (Odds, F. C., *CRC Crit. Rev. Microbiol.* 15:1-5 (1987)).

The most important species of microfungi which have been implicated as being involved in superficial or deep mycotic infections in the oral cavity include *Candida albicans, C. tropicalis, C. stellatoidea, C. pseudotropicalis, C. parapsilosis, C. quilliermondii, C. krusei,* and *C. vixwanathii,* all of which have been implicated in candidosis; *Torulopsis glabrata* which is the cause of torulpsidosis; *Geotrichum candidum,* which is the cause of geotrichosis; *Rhizopus, Mucor, Absidia,* and *Basidiobolus* which are the cause of aspergillosis, *Cryptococcus neoformans,* the cause of cryptococcosis; *Blastomyces dermatitidis,* the cause of blastomycosis; *Paracoccidioides brasiliensis,* the cause of paracoccidioidomycosis; *Sporothrix schenkii,* the cause of sporotrichosis; *Rhinosporidium seeberi,* the cause of rhinosporidoisis; *Histoplasma capsulatum,* the cause of histoplasmosis; *Histoplasma duboisii,* the cause of African histoplasmosis, *Coccidiodes immities,* the cause of coccidioidomycosis, *Trichophyton mentagrophytes, T. rubrum, T. tonsurans* and *T. violaceum,* the causes of dermatophytosis; and, *Rhinocladiella* or *Phialophora,* and *Cladosporium,* the causes of chromomycosis.

The Candida species is the most virulent of the fungi which infect the oral mucosa. Pathogenic Candida species are aerobic yeasts that can also grow anaerobically. *C. albicans,* the Candida species most often responsible for infections of the oral cavity, grows in two morphological forms: either as a budding yeast, or as a continuously extending hyphae which extends into tissue. In the oral cavity, Candida may cause a variety of disorders based on localization of the infection such as pulpitis, gingivitis, tonsillitis, cheilitis, glossitis, stomatitis, pharyngitis, laryngitis and sinusitis.

Oral candidosis has been classified into different categories based on the clinical and histopathological manifestations of the infection (Lehner, T., in *Clinical Aspects of immunology,* P.G.H. Gell, et al., eds., 3rd edition, Blackwell Scientific Publications, Oxford, 1975, pp.1387-1427).

Acute *Pseudomembranous candidosis,* or thrush, primarily affects children or patients with debilitating diseases (Crawson, R. A., *Dent. Res.* 15:361-364 (1965). *C. albicans* is a major causative agent of thrush in the newborn.

The clinical signs which usually appear first are creamy-white, soft, nonkeratotic plaques which appear on the mucosa of the tongue, cheeks, gum and pharynx. The plaque is easily rubbed off, leaving an inflamed mucosa underneath. There may be no subjective symptoms until the plaque spreads to the pharynx, larynx or esophagus, where it may cause dysphaghia, soreness and dryness of the tongue, a sore throat or symptoms of cheilitis.

Acute atrophic candidosis is a form of thrush which is consistently painful, and which is thought to arise as a consequence of the shedding of the fungal plaque from its site of attachment to the tissue. It can be found on the dorsum linguae, or associated with angular cheilitis and inflammation of cheeks and lips.

Chronic atrophic candidosis, or denture stomatitis is the term given to Candida-based infections of the denture-bearing tissues. *Torulopsis glabrata* is also associated with some forms of denture stomatitis.

Chronic mucocutaneous candidosis refers to four different types of candidosis which are resistant to treatment and which are associated with patients with a heterogeneous pattern of immunodeficiencies. These types of candidosis include chronic oral hyperplastic candidosis, which predominately affects adult males between the ages of 30 and 70; chronic localized mucocutaneous candidosis, which starts in childhood as an intractable oral Candida infection and later manifects itself as lesions in the nails, and skin of the fingers and toes; chronic localized mucocutaneous candidosis with granuloma which primarily affects young girls, starting in the mouth but later manifesting itself as horny masses of the face, scalp and upper respiratory tract; and, chronic localized mucocutaneous chadidosis with endocrine disorder, also found most frequently in young girls, and associated with lesions of the tongue, cheek, oral commissures and nails.

The establishment of a mycotic infection in the oral cavity presents a serious health problem to the host which must be treated and contained. Treatment of mycotic diseases is directed to controlling this flora.

The most widely used approach to date to control microfungi in the oral cavity has been mechanical cleaning methods such as brushing the teeth. Although this method has proved to be fairly successful in treating individuals, there is still a high recurrence rate. There is also the problem of motivating people to good oral hygiene habits that they will maintain throughout their lives.

Systemic administration of antimycotics per os or intravenously has been used to control mycotic infections, however, discontinuation of therapy often results in the return of the pathogens to the oral cavity. Long-term systemic antimycotic therapy in doses high enough to control oral infections are undesirable for treatment of oral infections because the potential dangers and side-effects associated with this form of treatment include the development of resistant strains and superimposed infections, gastrointestinal irritation, liver damage and neurological symptoms, among others.

Antifungal agents have also been used in the form of mouth rinses, dentifrices, solutions and gels but have not proven to be completely successful in preventing fungal infections. A main problem with these techniques is that the antifungal drug does not remain in the oral cavity long enough at efficacious levels.

Another serious problem with antifungal drugs is that they are by necessity directed towards controlling an infection by a eukaryotic fungal cell in a eukaryotic host. As a result, drugs effective against the fungus also tend to be toxic to the host. Thus it is important to develop methods which permit the localized, sustained application of the toxic drug in a manner and dosage which is efficacious but which minimizes toxicity the host. Especially, it is important to develop methods which use low doses of the drug.

A topical, sustained-release form of an antifungal agent, could help maintain a locally efficacious level of the antifungal drug in the oral cavity and prevent these side effects. Such a dosage form might also prevent undesirable systemic side effects by releasing the drug at a lower therapeutic level over a long period of time in a localized manner. Ridgway, F. et al.. U.S. Pat. No. 4,725,440, describes a soft, antifungal drug-containing pastille or troche which is free of rough edges and will not adhere to oral mucosa, but which only releases anti-fungal medications within the 15–90 minutes while it dissolves in the mouth.

Cyr et al., U.S. Pat. No. 3,312,594 describes long lasting troches or pastilles for the treatment of oral lesions which include an anhydrous adhesive based on pectin, gelatin and carboxymethylcellulose and which, when wetted, adhere to the oral mucous membranes. However, the Cyr formulation was not well-tolerated by patients (Ridgway, F. et al., U.S. Pat. No. 4,725,440).

Sustained release has been reported to be achieved by embedding chlorhexidine in an ethyl cellulose polymer to form a varnish (Friedman, M., et al., *J. Perio. Res.* 17:323–328 (1982); Friedman, M., et al., *IADR Prog. and Abstr.* 59:No. 905 (1980)). This dosage form was used in the local treatment of periodontal disease (Soskolne, W. A., et al., *J. Perio. Res.* 18:330–336 (1983)) and in the treatment of plaque prevention in patients wearing orthodontic appliances (Friedman, M., et al., *J. Dent. Res.* 64:1319–1321 (1985)). A drawback to this plaque preventative system was that although plaque accumulation was decreased by the application of a varnish composed of chlorhexidine embedded in an ethyl cellulose polymer, the effectiveness of the system in decreasing plaque accumulation was present only for a period of four days subsequent to administration of the varnish. Friedman et al., (*J. Dent. Res., supra*), concluded that "clearly the conditions in the oral cavity and the formulation used do not, at present, facilitate such prolonged prevention of plaque accumulation." These authors also suggested that by altering the varnish components and method of preparation it might be possible in clinical use to sustain the necessary level of antibacterial agent release for longer periods. No suggestion was made in this publication as to how this could be accomplished.

Mastic has been used previously for dental purposes. U.S. Pat. No. 4,668,188 (Wolfenson, G. B.) discloses the use of a curable mastic in the production of an oral impression tray for making impressions of teeth and jaw structures. Mastics have been used in the production of dental molds (VonWeissenfluh, H. U.S. Pat. No. 4,500,288), as an adhesive to secure dental articulators (U.S. Pat. Nos. 4,548,581 and 4,382,787, Hoffman, R. E.) and as a tooth decay preventative (Wahmi U.S. Pat. No. 4,374,824). U.S. Pat. Nos. 4,532,126 and 4,428,927 (Ebert, W. R., et al.) disclose chewable, filled, one-piece soft elastic gelatin capsules, made chewable by a masticatory substance, such as a synthetic mastic.

U.S. Pat. No. 4,459,277 (Kosti, C. M.) relates to novel plaque compositions for use in evaluating oral hygiene practices. In brief, the patent discloses a water-insoluble, water-immiscible dye emulsified in fine droplets or rupturable capsules. The patent discloses the use of mastic resin as well as alginates, and other gums as an insoluble media for dye dispersion. In particular, sodium carboxymethylcellulose is disclosed. Also disclosed is the possibility of incorporating antibacterial agents such as stannous fluoride into the compositions. Significantly, the Kosti patent is concerned with diagnostic rather than therapeutic applications. The patent fails to suggest compositions exhibiting long-term preventive activity.

The background art fails to identify any compositions of matter comprising an effective antifungal agent together with a long-term sustained-release carrier, in combination with an adhesive polymer such as a mastic and a plasticizer such as polyethylene glycol, for use as an antifungal preventative varnish in the oral cavity by humans and other animals, under conditions in which the antimycotic agents have no deleterious medical side effects, and do not cause staining of the teeth. Another highly desirable characteristic not found in the art of record is that the antifungal agent should be released from the composition, not only in a sustained fashion, but over a sufficiently long period of time so as not to require excessive application of the composition.

SUMMARY OF THE INVENTION

With this need in mind, the present inventor set out to find an oral antimycotic preventative composition which contains an antifungal agent effective against those microfungi that are responsible for oral infections, said composition being such that the antifungal agent can be released at efficacious levels in a sustained, long-term fashion, and such that the antifungal composition has the property of long-term adhesion to the oral tissue and teeth, and such that the antifungal composition remains plastic during the entire period of application. With this goal in mind, the inventor has discovered an antifungal preventative composition with these desirable characteristics, the composition comprising an antifungal agent embedded in a sustained release carrier composed of a cellulose polymer, in a pharmaceutically acceptable vehicle, optionally containing a plasticizer such as polyethylene glycol and/or an adhesive polymer such as gum mastic.

DETAILED DESCRIPTION OF THE PREFERRED EMBODIMENTS

This invention relates to oral compositions that provide sustained, efficient, inexpensive, localized antifungal activity in the oral cavity at efficacious levels without deleterious side effects, and methods for using such compositions.

By "oral cavity" is meant the mouth and the surrounding esophageal area. Therefore, for example, the oral cavity includes the tongue, gums, palate, throat, teeth, tonsils and periodontal tissue.

By "sustained-release" is meant the continuous release of an active substance at efficacious levels for a prolonged period of time, such as 2–4 weeks or longer. The release of the active substance may be constant or pulsed, as long as efficacious levels of the active substance are provided to the surrounding milieu for the desired period of time.

By an "efficacious level" is meant a level or concentration of a drug or other active agent which is high enough to be effective in treating the condition the drug was designed to treat.

By "oral varnish" is meant a composition which is topically applied to a hard surface such as a tooth or orthodontic appliance and which dries as a film adhering to that surface, in a manner which resists removal under normal conditions, such as eating or brushing the teeth.

The compilation of the components of the aforementioned oral composition is based upon the specific properties of each of the individual components, wherein each component of the combination increases the antifungal effectiveness of other members of the combination.

The oral composition of the invention assists in the prevention of microfungal infections of the oral cavity and periodontal tissue, and in the relief of symptoms resulting from existing microfungally-caused problems, by attacking the pathogenic yeast and fungi responsible for the infection in the oral cavity. A variety of antifungal agents are suitable for the present invention. Preferred are the polyene antifungals, especially nystatin and amphotericin B. Examples of other antifungal agents applicable to the methods of the invention include 5-fluorocytosine and imidazole- and triazole-derivative antifungal agents, especially naftifine, terbinafine, tolnaftate, tolciclate, isoconazole, sulconazole, miconazole, clotrimazole, econazole, bifonazole, oxiconazole, thioconazole, ketoconazole, itraconazole, fluconazole, and terconazole, all known to the art. See, for example, Kostiala, I. et al., *Acta Odontol. Scand.* 37;87–101 (1979); and Bossche, H. V., CRC Crit. Rev. Mircobiol. 15:57–72 (1987).

In another embodiment, combinations of more than one antifungal agent are used in the composition of the invention. Combinations of antifungal agents can be prepared, for example, for the purpose of providing treatment or protection against a broad spectrum of microfungal species, or for the purpose of attacking a specific microfungal species with drugs acting through different modes of action. Combination of antifungal agents may also allow a lower dose of a given antifungal agent to synergistically act with a lower dose of another antifungal agent in a manner which is efficacious in combination but not separately.

The antimycotic composition may be formulated to include other drugs such as antibacterial or antiseptic agents known to the art. See, for example, the section on "Quaternary Ammonium and Related Compounds" in the article on "Antiseptics and Disinfectants" in Kirk-Othmer Encyclopedia of Chemical Technology, 2nd ed. (Vol. 2, pp. 632-5), incorporated herein by reference. Such materials have been sued in oral compositions to counter bacteria in the oral cavity. Among the most common and efficacious of these antibacterial, quaternary ammonium compounds are cethylpyridinium chloride and benzalkonium chloride. Other cationic ammonium antibacterial agents of this type are mentioned, for instance, in U.S. Pat. Nos. 2,984,639, 3,325,402, 3,431,208, 3,703,583, and 4,339,430, British Patent No. 1,319,396, and German Patent No. 2,332,383. Most preferred is cetylpyridinium chloride, which is efficacious, compatible with the other components of the oral composition, and inexpensive by virtue of being a non-prescription drug. None of these compounds has been used before in sustained release, long-acting compositions. By long acting is meant a composition which provides efficacious levels o the active drug contained therein for a period of weeks, preferably at least 4 weeks, or 30 days.

It is also a feature of this invention that the aforementioned antifungal agent is released to the sites of fungal lesions and pockets in a long-term sustained release manner so as to reduce the required frequency of use. Long-term sustained release is desirable because it improves patient compliance with the treatment protocol and it is more convenient for the patient. Hence the success of the treatment is more probable. The method of the invention needs only a single application of the oral varnish composition of the invention to remain efficacious for a period of weeks. Other methods require a multi-dose application of paste every few days or ingestion of lozenges every four hours by the patient. At best, the pastes remain effective for 2–3 days and the lozenges only for hours.

In addition, by the composition and method of the invention, because of the long-term sustained release of the drug, much lower amounts of the antifungal drug are required for efficacious results. Conventional therapy uses doses of nystatin as high as $10^8 IU$/dose. The concentrations of nystatin preferred in the invention are $2 \times 10^5$ I.U., with an acceptable range of $2 \times 10^5 - 10^6$ I.U. Because of the lower doses of nystatin, the side effects of the drug are eliminated or minimized. For example, at the efficacious concentrations of nystatin taught by the compositions and methods of the invention, in clinical evaluations there was no bitter-taste noted. The bitter taste of the drug is one of the major complaints of patients taking conventional nystatin therapy.

Lastly, the physical form and manner of presentation of the composition of the invention is highly advantageous for a patient with an oral microfungal infection. Often the area of the infection is so sore so as to make the direct application of a paste or even sucking lozenges, troches or pastilles very painful; rinsing with a mouthwash does not leave efficacious levels of the drug in the oral cavity. In other cases, oral treatments with mouthwashes, lozenges, pastes, troches or pastilles is very difficult or just not practical, for example with infants or animals. The compositions and methods of the invention solve this problem by applying the antifungal drug to the teeth, gingival tissues or orthodontic appliance, for slow, long-term sustained release at efficacious levels into the salival fluids of the oral cavity. In addition the composition of the invention is colorless and visually undetectable by those unaware of the treatment.

Long term sustained release is accomplished by embedding the active drug agent(s) in a polymer. The specific polymer used is not critical. Long term sustained release, may, in accordance with the present invention, be accomplished by embedding an anti-fungal agent in any biologically suitable polymer. For example, a hydrophobic polymer, a hydrophilic polymer, or a combination of hydrophilic and hydrophobic polymers, may be used to form sustained releases formulations that would be suitable as a varnish for oral administration in accordance with the present invention. One or more proteinaceous polymers (such as gelatin, etc.), cellulosic polymers, acrylic polymers, etc. may be employed. Suitable polymers are disclosed in U.S. patent applications Ser. Nos. 07/189,918; 07/304,091; 07/369,223; and 07/432,667; which applications are herein incorporated by reference in their entirety.

Cellulosic or acrylic polymers are especially preferred for forming a varnish for oral administration. The use of these polymers provides the advantage of allowing lower doses of a drug to be used and thus eliminating or minimizing side effects such as staining of teeth and dentures and unpleasant taste. A variety of suitable hydrophobic polymers are known in the art of oral compositions. Preferred are the insoluble and inexpensive polymers: hydrophobic type (poly-ethylene, polymethacrylate, polyamide-nylon, poly(ethylene-vinyl acetate) cellulose nitrate, silicones and others). Most preferred is ethyl cellulose. Another suitable polymer is methylacrylic acid polymer.

The composition of the invention is preferably applied to teeth or dental appliances which act as a solid support and point of release for the antifungal agent in the composition throughout the treatment period. The tooth or orthodontic appliance varnished with the antifungal composition of the invention may be placed in direct contact with the site of infection, as for example, by placing dentures on top an infected or irritated gum for the treatment of denture stomatitis. Alternatively, the varnished tooth or dental appliance may act as a reservoir which releases efficacious levels of the antifungal agent in the salival fluids to other infected sites within the oral cavity or throat. Therefore, in a highly preferred embodiment, there is direct contact between the composition of the invention and the site of microfungal infection. In another preferred embodiment, the composition of the invention is applied to a site removed from the infected area but within the range of the efficacious levels of antifungal drugs released by said composition. Orthodontic appliances within the scope of the invention include dentures, bridges, braces, anchoring pins and the like. The appliance can be a temporary or permanent appliance. The compositions and methods of the present invention therefore provide a therapy for denture stomatitis, oral thrush, and other oral fungal diseases and conditions.

Thus, in a preferred embodiment, an oral composition with the highly desirable characteristics mentioned above comprises an antimycotic compound such as nystatin embedded in a sustained release cellulosic polymer such as ethyl cellulose, in a pharmaceutically effective vehicle. For example, nystatin, 100,000 IU (1-5 parts), and ethyl cellulose (5-9 parts) may be dissolved in ethanol (80 -120 parts) for the preparation of sustained release varnish in film form.

For application to buccal and lingual surfaces of teeth, an ethanolic solution of the antimycotic agent and cellulosic polymer (containing up to 4% of the drug as used in the varnish) are applied with a soft brush or with a spray. Ethanol may be evaporated by a gentle stream of warm air. Mouthwash forms are not suitable because of inefficient application of the composition to affected tissue areas. However, orthodontic appliances such as dentures may be dipped in a solution containing the composition of the invention.

For application to orthodontic appliances, a total of about 40 mg of antimycotic agent such as nystatin or amphotericin B in an ethanolic solution with ethyl cellulose may be applied per appliance by dipping, spraying or painting it on with a soft brush, and residual solvent removed with a gentle stream of warm air.

Those skilled in the treatment of diseases of the oral cavity will, without undue experimentation, be able to produce ranges of concentrations of other appropriate antifungal agents and sustained release polymers.

The thickness of the film as varnish can be varied according to the desired length of efficacious treatment or drug potency. In a preferred embodiment the film coating the tooth or appliance is 10–300 μm thick.

It is another feature of the invention that the oral compositions for treatment and prevention of fungal infections also provide for additional desirable components. For example, the adhesiveness of the oral composition may be improved by the incorporation within said composition of gums such as gum mastic in a formulation providing from 1–20% by weight of the gum mastic. Other suitable mastics are disclosed in Heyd, D., et al., U.S. Pat. No. 4,315,779 and Wahmi, H.V.R., et al. U.S. Pat. No. 4,374,824.

In another formulation, other compositions may include demulcents/humectants (i.e., plasticizers) such as polyethylene glycol 400-to-4000, glycerol, sorbitol, or mineral oil in concentrations of about 1% by weight. Other humectants, detergents, or surface-active agents will be known to those skilled in the formulation of oral compositions.

Thus, in a preferred composition, the oral composition of the invention comprises nystatin, ethyl cellulose polymer, an adhesive, a plasticizer, and solvent (i.e., aqueous ethanol). In a highly preferred formulation, gum mastic is also present. Water, flavorings, and coloring agents may also be present as required. Once applied to teeth or other orthodontic appliance, the varnish is not easily removed by normal dental hygiene protocols, such as brushing. The dry film can only be removed mechanically. In addition, because the varnish coats the surface of the teeth or orthodontic support with a smooth surface and the same contours of the support, it adds no uncomfortable, unfamiliar or otherwise annoying geometry to the oral cavity, in the manner that a paste can.

The composition and methods of the invention may also be applied as a preventative or deterrent measure, especially in patients highly susceptible to opportunistic infections of the oral cavity by microfungi.

The varnish of the invention may also be applied extraorally to sites of microfungal infection, for example, to infected nails on the fingers and toes of patients with chronic mucocutaneous candidosis. Alternatively, the composition of the invention, especially in combination with antibacterial agents, may be provided on a varnished pad or bandage or patch which is placed in contact with the site of infection, for example, topically or intravaginally.

Having now generally described the invention, the same will become better understood by reference to certain specific examples which are included herein for purposes of illustration only and are not intended to be limiting unless otherwise specified.

EXAMPLE 1

Varnish Preparation

The following formulations (Table 1) were all prepared by the same general procedure as follows: ethyl cellulose and polyethylene glycol polymers were dissolved in the suitable solvent. After complete dissolution of the polymers, the additional components of the varnish are added.

EXAMPLE 2

Evaluation of the Varnish in Vitro Sustained Release Activity of Nystatin on Candida Albicans in Vitro Films containing Nystatin were cast from the varnish formulation IV on glass plates using the technique of Kanic et al., *J. Pharm. Sci.* 51:77 (1962). The solvent was allowed to evaporate at room temperature and the residual film removed from the plate. A strain of *C. albicans* isolated from clinical material was used in this study. A 1:10 dilution of an overnight growth stock suspension of the above organism was mixed with mycological culture medium (Sabourand) and poured into petri dishes. Five mm diameter disks of the films containing Nystatin were placed on the hardened medium.

After 24 h or 48 h, films were transferred onto another set of petri dishes containing the same medium plus *C. albicans* suspension as in the first set.

Inhibition zones were recorded after incubation periods of 24 and 48 h at 37° C. All films were used in duplicate. The mean inhibition zone is summarized in Table 2.

EXAMPLE 3

Clinical Study: Evaluation of the Varnish in vivo

Preparation of coated denture. The Nystatin varnish (Formulation IV) was applied to the denture base facing the mucosa, by means of a soft brush. Removal of the solvent was achieved by a gentle stream of hot air.

The dentures were weighted before and after coating and the total amount of coating calculated. Forty mg of Nystatin per denture was the average amount of drug used. (Equivalent to 200,000 I.U.)

In the preliminary clinical evaluation of the system, 5 patients suffering from denture stomatitis were selected from an old age home. Three tests were performed on each patient: a) 1 swab from upper gum, b) 1 swab from denture, and c) 2 ml of saliva was collected.

Material from the swabs was washed into a solution containing 0.2% neopeptone + 0.8% Tween 80, which was also used for further dilution of this material and of the saliva. Ten ml aliquots of the various dilutions were inoculated in duplicate onto plates containing bacteriological blood agar (for bacterial isolation) and plates containing mycological medium Sabourand (for *C. albicans* isolation).

All plates were incubated for 48 h at 37° C. and the number of bacterial and yeast colonies recorded.

The effects of the local application of a sustained-release delivery system of nystatin on fungal growth due to denture stomatitis in these patients are summarized in Table 3.

In summary there was an improvement in clinical status of the disease was observed, total elimination of Candida in saliva, gum and denture with no change in the normal bacteria flora levels. There was an improved compliance on the part of the patient; one single application is a much more convenient way of treatment compared to the conventional multi-dose application, and this new way of treatment is not dependent on the patient's cooperation.

Much lower amounts of Nystatin are necessary for the clinical effect as compared to the total of $10^8$ I.U. used in conventional therapy. Lastly, no side effects, such as the bitter taste of Nystatin were observed in the preliminary clinical evaluation of this system These results are consistent with inhibition of fungal growth in the oral cavity of these patients by this form of the drug and further suggest that efficacious concentrations of the drug on the tooth/tissue surface is achieved creating a local antimycotic effect.

TABLE 2

| Inhibition Zone of Candida Growth by Sustained Release Films Containing Nystatin | | | | | | | | | | | | | | | | |
|---|---|---|---|---|---|---|---|---|---|---|---|---|---|---|---|---|
| Time (days) | | | | | | | | | | | | | | | | |
| 1 | 2 | 3 | 4 | 5 | 7 | 9 | 11 | 13 | 15 | 17 | 19 | 21 | 23 | 25 | 27 | 29 | 31 |
| Inhibition zone (mm) | | | | | | | | | | | | | | | | |
| 20 | 17 | 17 | 12 | 11 | 12 | 13 | 13 | 11 | 11 | 10 | 12 | 10 | 10 | 9 | 10 | 9 | 9 |

There was no inhibition of Candida growth in control samples containing ethyl cellulose films only.
The measurements of inhibition were discontinued after 31 days.

TABLE 3

| THE REDUCTION OF CANDIDA IN DENTURE WEARERS AFTER SINGLE APPLICATION OF SUSTAINED RELEASE VARNISH OF MYSTATIN | | | | | | | | | |
|---|---|---|---|---|---|---|---|---|---|
| | | 0 | | 2 days | | 3 days | | 7 days | |
| Patient | | Bacteria* | Candida*[(1)] | Bacteria | Candida | Bacteria | Candida | Bacteria | Candida |
| 1 | G | $7.1 \times 10^8$ | 1.0 | $7.1 \times 10^7$ | 0 | $1.2 \times 10^6$ | 0 | $8.2 \times 10^6$ | 0 |
| | D | $5.5 \times 10^7$ | 2.9 | $1.2 \times 10^8$ | 0 | $8.0 \times 10^7$ | 0 | $6.3 \times 10^7$ | 0 |

TABLE 3-continued

THE REDUCTION OF CANDIDA IN DENTURE WEARERS AFTER
SINGLE APPLICATION OF SUSTAINED RELEASE VARNISH OF MYSTATIN

| Patient | | Bacteria* 0 | Candida*[1] 0 | Bacteria 2 days | Candida 2 days | Bacteria 3 days | Candida 3 days | Bacteria 7 days | Candida 7 days |
|---|---|---|---|---|---|---|---|---|---|
|   | S | $5.5 \times 10^7$ | 2.4 | $4.1 \times 10^7$ | 0.25 | $7.5 \times 10^7$ | 0.9 | $2.2 \times 10^8$ | 1.6 |
| 2 | G | $2.2 \times 10^6$ | 28.8 | $2.0 \times 10^6$ | 0 | $1.1 \times 10^7$ | 0 | $5.1 \times 10^6$ | 0 |
|   | D | $4.1 \times 10^6$ | 19.9 | $4.1 \times 10^6$ | 0 | $1.2 \times 10^6$ | 0 | $3.2 \times 10^6$ | 0 |
|   | S | $1.4 \times 10^8$ | 21.1 | $1.2 \times 10^7$ | 5.2 | $1.1 \times 10^7$ | 3.0 | $2.3 \times 10^7$ | 6.1 |
| 3 | G | $3.3 \times 10^7$ | 16.2 | $3.2 \times 10^7$ | 0 | $3.1 \times 10^7$ | 0 | $8.0 \times 10^7$ | 0 |
|   | D | $2.6 \times 10^7$ | 11.8 | $2.4 \times 10^7$ | 0 | $1.2 \times 10^7$ | 0 | $2.3 \times 10^7$ | 0 |
|   | S | $3.1 \times 10^7$ | 10.1 | $1.0 \times 10^7$ | 6.1 | $2.2 \times 10^7$ | 2.4 | $8.6 \times 10^6$ | 2.0 |
| 4 | G | $4.2 \times 10^7$ | 6.5 | $4.4 \times 10^7$ | 0 | $8.1 \times 10^7$ | 0 | $6.2 \times 10^7$ | 0 |
|   | D | $6.2 \times 10^7$ | 9.2 | $7.1 \times 10^7$ | 0 | $1.2 \times 10^8$ | 0 | $7.2 \times 10^6$ | 0 |
|   | S | $2.1 \times 10^8$ | 4.2 | $5.2 \times 10^7$ | 2.6 | $6.1 \times 10^7$ | 1.8 | $9.0 \times 10^7$ | 2.0 |
| 5 | G | $4.2 \times 10^7$ | 12.6 | $8.0 \times 10^6$ | 0 | $2.2 \times 10^7$ | 0 | $2.1 \times 10^7$ | 0 |
|   | D | $7.2 \times 10^7$ | 17.2 | $6.2 \times 10^6$ | 0 | $6.1 \times 10^6$ | 0 | $1.6 \times 10^7$ | 0 |
|   | S | $5.2 \times 10^6$ | 10.8 | $3.2 \times 10^6$ | 2.8 | $6.4 \times 10^6$ | 5.2 | $2.0 \times 10^7$ | 4.3 |

*Candida and Bacteria determined from the same sample

[1] Calculated from $\frac{\text{Candida counts}}{\text{Bacteria counts}} \times 10^4$ G Gum
D Denture
S Sputum

Having now fully described the invention, it will be understood by those with skill in the art that the scope may be performed within a wide and equivalent range of conditions, parameters and the like, without affecting the spirit or scope of the invention or any embodiment thereof.

What is claimed is:

1. A sustained release oral anti-fungal varnish composition which comprises:
   (a) efficacious levels of an antimycotic drug;
   (b) a sustained release hydrophobic polymer, wherein said sustained release hydrophobic polymer is selected from the group consisting of polyethylene, polymethacrylate, polyamide-nylon, poly(ethylene-vinyl acetate) cellulose nitrate, and silicones and
   (c) a plasticizer;
in a pharmaceutically acceptable vehicle.

2. The varnish composition of claim 1, wherein said antimycotic drug is selected from the group consisting of nystatin, amphotericin, B, miconazole, and clotrimazole.

3. The varnish composition of claim 2, wherein said antimycotic drug is nystatin.

4. The varnish composition of claim 2 wherein said atimycotic drug is Amphotericin B.

5. The varnish composition of claim 1, wherein said pharmaceutically acceptable vehicle comprises an agent selected from the group consisting of water; ethyl alcohol; and ethyl alcohol and water.

6. The varnish composition of claim 5, which additionally contains an agent selected from the group consisting of a flavoring agent, surface active agent and coloring agent.

7. The varnish composition of claim 1, wherein said plasticizer is selected from the group consisting of polyethylene glycol, glycerol, sorbitol, and mineral oil.

8. The varnish composition of claim 5, which additionally contains an adhesive gum.

9. The varnish composition of claim 8, wherein said adhesive gum is gum mastic.

* * * * *

UNITED STATES PATENT AND TRADEMARK OFFICE
CERTIFICATE OF CORRECTION

PATENT NO. : 5,116,603

DATED : May 26, 1992

INVENTORS : Michael Friedman

It is certified that an error appears in the above-identified patent and that said Letters Patent is hereby corrected as shown below.

ON the title page, item [56], under "U.S. Patent Documents", delete "3,394,001" and insert therefor --3,934,001--.

On the title page, item [56], under "Foreign Patent Documents", after "990957 5/1965 United Kingdom", insert therefor on the next line --55397 1/1981 Europe--.

At column 6, line 16, delete "sued" and inset therefor --used--.

At column 9, after line 25 and before "Example 2", insert therefor

--Ethyl cellulose - EC
Polyethylene glycol - PEG
Nystatin - NYS

TABLE 1

MATERIAL/FORMULATION

| | I | II | III | IV | V | VI | VII | VIII | IX | X |
|---|---|---|---|---|---|---|---|---|---|---|
| NYS (G) | 1.5 | 2.0 | 3.0 | 3.0 | 3.0 | 3.0 | 3.0 | 3.0 | 3.0 | 4.0 |
| EC-NF100 (G) | 8.5 | 7.0 | 6.0 | 6.0 | 6.0 | 5.0 | 6.0 | 6.0 | 6.0 | 6.0 |
| PEG 400 (G) | 0.5 | 1.0 | 1.0 | 1.0 | 1.0 | 1.0 | --- | --- | --- | --- |
| PEG 4000 (G) | --- | --- | --- | --- | --- | --- | 1.0 | 1.0 | --- | --- |
| GUM MASTIC | --- | --- | --- | --- | --- | 1.0 | --- | --- | 1.0 | --- |
| ETHANOL (C"C) | 100 | 100 | 100 | 80 | 120 | 100 | 100 | 100 | 100 | 100 |

--.

UNITED STATES PATENT AND TRADEMARK OFFICE
CERTIFICATE OF CORRECTION

PATENT NO. : 5,116,603

DATED : May 26, 1992

INVENTORS : Michael Friedman

It is certified that an error appears in the above-identified patent and that said Letters Patent is hereby corrected as shown below.

At column 9, line 33, delete "Kanic" and insert therefor --Kanig--.
At column 10, line 63, delete "Mystatin" and insert therefor --Nystatin--.
At column 12, line 3, delete "Mystatin" and insert therefor --Nystatin--.
At column 12, line 23, delete "amphotericin, B," and insert therefor --amphotericin B,--.
At column 12, line 28, delete "atimycotic" and insert therefor --antimycotic--.

Signed and Sealed this

Eleventh Day of May, 1999

*Attest:*

Q. TODD DICKINSON

*Attesting Officer*     *Acting Commissioner of Patents and Trademarks*